United States Patent [19]

Harrington et al.

[11] Patent Number: 4,867,404

[45] Date of Patent: Sep. 19, 1989

[54] FLEXIBLE HOLDER FOR A CYSTOSCOPE OR THE LIKE

[75] Inventors: Frank S. Harrington, Catonsville, Md.; Michael J. Manyak, Washington, D.C.

[73] Assignee: The United States of America as represented by the Department of Health and Human Services, Washington, D.C.

[21] Appl. No.: 197,096

[22] Filed: May 16, 1988

[51] Int. Cl.⁴ ............................................. E04G 3/00
[52] U.S. Cl. ............................... 248/231.4; 248/276; 248/316.4; 128/20; 24/523
[58] Field of Search ................ 248/276, 231.4, 316.4; 24/136 B, 135 R, 569, 523, 525; 128/20

[56] References Cited

U.S. PATENT DOCUMENTS

| | | | |
|---|---|---|---|
| 624,211 | 5/1899 | Hill | 24/569 X |
| 2,061,718 | 11/1936 | Stahl | 24/523 X |
| 2,482,625 | 9/1949 | Kunkel | 24/523 |
| 2,497,820 | 2/1950 | Kielland | 24/523 X |
| 3,040,739 | 4/1962 | Grieshaber | 128/20 |
| 3,222,053 | 12/1965 | Severdia | 24/523 X |
| 3,334,854 | 8/1967 | Nesbitt | 248/316.4 |
| 3,384,077 | 5/1968 | Gauthier | 128/20 |
| 3,469,810 | 9/1969 | Dorris | 24/525 X |
| 3,747,170 | 7/1973 | Kieves | 24/523 X |
| 3,858,578 | 1/1975 | Milo | 128/20 |
| 4,239,036 | 12/1980 | Krieger | 128/20 |
| 4,457,300 | 7/1984 | Budde | 128/20 |
| 4,461,284 | 7/1984 | Fackler | 128/20 |
| 4,467,791 | 8/1984 | Cabrera et al. | 128/20 |
| 4,573,452 | 3/1986 | Greenberg | 128/20 |
| 4,616,384 | 10/1986 | Lowell et al. | 24/335 |
| 4,616,797 | 10/1986 | Cramer | 248/230 |
| 4,617,916 | 10/1986 | Levahn et al. | 128/20 |

FOREIGN PATENT DOCUMENTS 2031281 3/1979 United Kingdom .

Primary Examiner—Ramon S. Britts
Assistant Examiner—David G. Kolman
Attorney, Agent, or Firm—Browdy and Neimark

[57] ABSTRACT

A flexible holder and clamping assembly for adjustably holding cystoscopes or other endoscopic instruments and retractors or the like adjacent to or on an examination tables or the like is equipped with a unique clamping assembly which permits the holding of various sized instrument shafts. The clamping assembly is equipped with a vertically adjustable spring-biased C-shaped, open-sided region which is urged into a normally open position. The instrument shaft is, after positioning relative to the patient, slid sideways into the C-shaped jaw and retained between the jaw and a pair of circumferentially opposing notches of a tubular housing. The clamp also includes a head portion having various openings and a cavity for receiving the parts and connections of the clamping assembly.

15 Claims, 2 Drawing Sheets

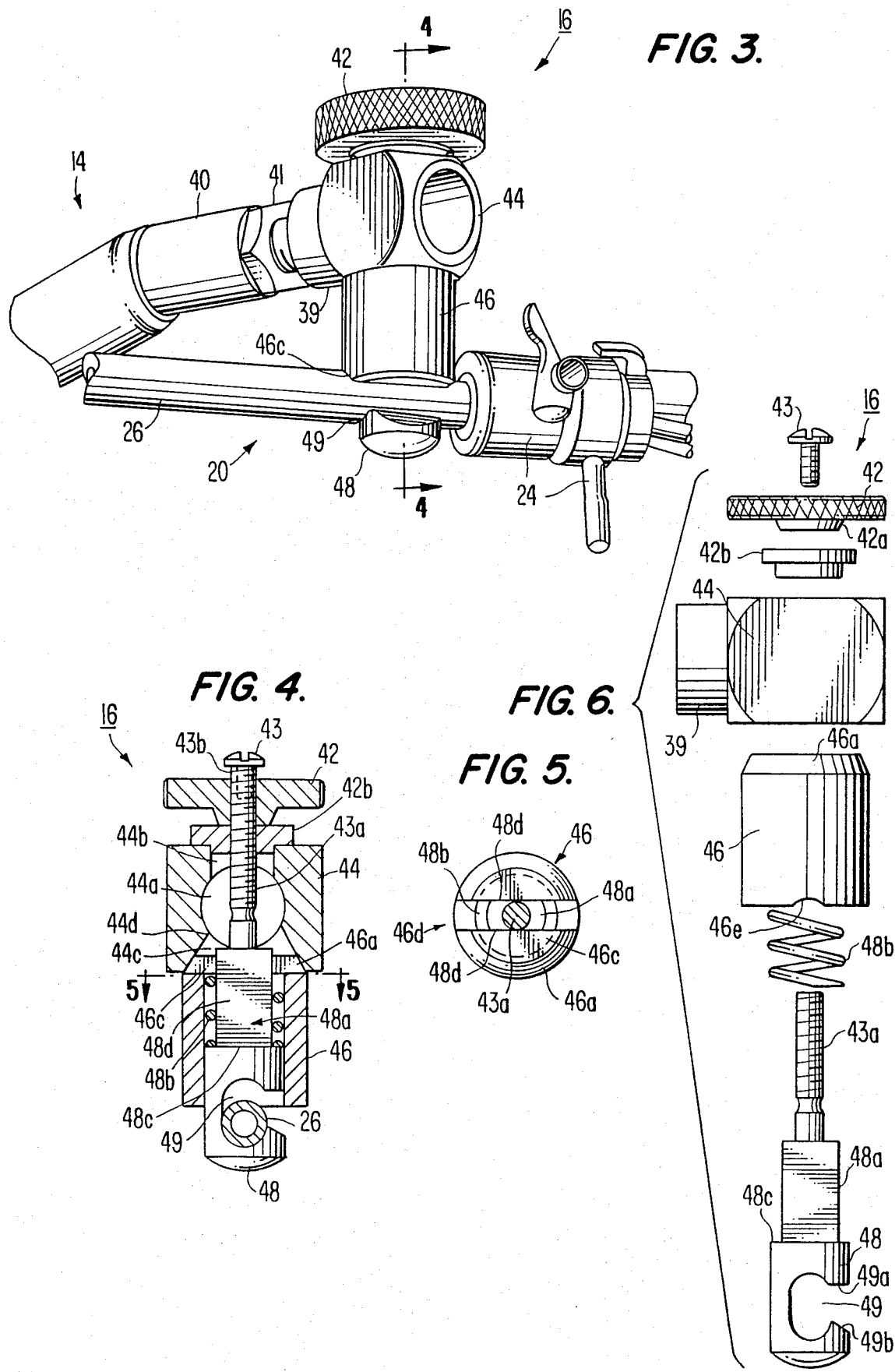

FLEXIBLE HOLDER FOR A CYSTOSCOPE OR THE LIKE

FIELD OF THE INVENTION

The present invention relates to improvements in diagnostic and surgical procedures, and especially to flexible holders for the stabilization of cystoscopes or other endoscopic instruments or surgical retractors used during diagnostic or surgical procedures. More particularly the invention relates an improved holder clamp which may be situated near the operating or examination table for supporting an endoscope, a retractor or the like after same has begun to have been used in conjunction with a patient.

BACKGROUND OF THE INVENTION

Stabilization of endoscopic equipment during a procedure may be desirable under a variety of circumstances. Colonoscopy is made easier by a stand that supports the weight of the scope, which allows for increased freedom of the hands for manipulation. Surgical manipulation during laparoscopy also is aided by stabilizing the instruments. Other instrument holders have been devised to keep endoscopic instruments untangled and secure on or near the operating table.

In urological practice ureteral catheter or stent placement and routine stone manipulation are facilitated by endoscopic stabilization. A stable cystoscope decreases, radiation exposure to the physician who performs retrograde pyelography by increasing the distance from the radiation source during injection of the contrast agent. Photography is aided by anchoring the cystoscope, as well as visualization of pathological conditions by a succession of students, residents or colleagues. Photodynamic therapy, in which constant light distribution to the bladder mucosa during several minutes is necessary, requires stabilization of the cystoscope.

Several means have been used to stabilize endoscopic equipment, including a variety of stationary adjustable stands and flexible coiled instruments. When no cystoscope holder is available a sling constructed from a surgical towel has been used. Most of these devices are less than ideal because they frequently are awkward or only transiently stable.

Thus, the stabilization of an endoscope during an examination procedure or a retractor during surgery is frequently necessary and presents problems for the physician or surgeon. Most attempts to support endoscopes require holders and supporting arrangements which restrict the physician's mobility to manipulate the instrument to desired locations once the instrument has been positioned. The same problems exist with other instruments, including retractors, during surgery. Over the years, many attempts have been proposed in the patent literature to overcome this cumbersome problem of stability. For example, the U.S. Pat. Nos. 4,457,300 to Budde and 4,573,452 to Greenberg disclose surgical holders for supporting retractors and laparoscopes, respectively. Both of these holders utilize flexible supporting posts or arms for facilitating some movement of the medical equipment during the respective procedures. However, while these flexible posts or arms permit movement of the particular instruments, neither of these holders employ clamps with a sufficient degree of movement and/or rotation and which can accept instruments therein without considerable difficulty. Thus, while these devices are useful, they nevertheless restrict the ease with which a surgeon or physician can mount the instrument to the support once use of the instrument has begun.

The patent to Greenberg employs a clamp 70 at the distal end of the flexible member 60 through which, apparently, the laparoscope 10 must be threaded prior to use thereof (See col. 4, lines 28-33). In other words, the clamp 70 does not easily permit subsequent attachment to the laparoscope after the laparoscope has been positioned within the abdomen. In practice, however, it is very inconvenient to try to manipulate such an instrument, or a cystoscope or retractor, with extraneous equipment affixed to or near the proximal end, and invariably the surgeon or physician will first try to manipulate the instrument while it is unencumbered and then later try to clamp it into position, which apparently cannot be done with the Greenberg construction.

Other types of clamps having movable jaws have the tendency to crush or damage the instrument which it is trying to support, and this is especially likely when actions must be taken quickly. This leads to the damage or destruction of some very expensive instruments. In some cases clamps for such instruments can be used for instruments of only one diameter. Also, prior devices have limited degrees of movement or rotation. Patent literature showing such other clamps for surgical instruments and retractors include the patents to Grieshaber 3,040,739; Gauthier 3,384,077; Fackler 4,461,284 and LeVahn et al 4,617,916, but these constructions have not solved the aforementioned problems.

Other clamps have been designed for special purposes, such as for supporting tubular members without the necessity of using rotatable lever/movable jaw structures. For example, the U.S. Pat. Nos. 2,061,718 to Stahl; 2,482,625 to Kunkel; 4,616,384 to Lowell et al and 4,616,797 to Cramer all show adjustable clamps using spring-biased members to urge the device to be supported against or within a channel cavity. The Patents to Stahl, Cramer, and Lowell et al all require the use of turnable knobs or levers to aid in the manipulation of the clamp. The Kunkel clothes pin has a proximal jaw, spring-biased to the fully closed position relative to its distal jaw and must be urged open to accept a device to be clamped. These above-mentioned patents are neither designed nor suited for holding delicate and expensive surgical instruments.

No surgical instrument holder and clamp therefor has previously been available for holding cystoscopes or other endoscopic devices or surgical retractors that may be attached readily and locked or anchored in place after positioning relative to the patient, and which also may accommodate various sized instruments. There is a great need for a surgical holder having a clamp of greater versatility during endoscopic and surgical procedures, and which will allow for a firm but delicate grasp of fiber optic instruments and which will facilitate instrument rotation of 360 degrees along two axes.

SUMMARY OF THE INVENTION

Accordingly, it is an object of the present invention to overcome disadvantages and deficiencies of the prior art, such as set forth above.

It is another object of the present invention to facilitate certain surgical and diagnostic procedures.

It is still another object of the present invention to provide an improved flexible holder for cystoscopes, other endoscopic devices, retractors, and the like.

It is a further object of the present invention to provide a flexible holder having a spring-biased clamping arrangement that works in a convenient manner.

It is yet another object of the present invention to provide a flexible holder having a clamp which will allow for a firm but delicate grasp of a cystoscope, retractor or the like.

It is still a further object of the present invention to provide a flexible holder for endoscopes and retractors having a clamp which may readily receive and stabilize an instrument after positioning of the instrument on or relative to a patient.

It is yet a further object of the present invention to provide a clamp for a flexible surgical holder having the ability to rotate 360 degrees upon two axes.

It is still a further object of the present invention to provide a clamp for a flexible surgical holder having an opensided configuration, the clamp being adapted to accommodate various sized cystoscopes or the like.

It is still another object of the present invention to provide a clamp for a flexible surgical holder which will permit users greater instrument versatility during endoscopic or surgical procedures.

It is still a further object of the present invention to provide a flexible surgical holder and clamp therefor which is relatively inexpensive to manufacture and which is especially easy and simple to manipulate.

Still other objects, features and attendant advantages of the present invention will become apparent to those skilled in the art from the following detailed description of certain exemplary embodiments constructed in accordance therewith, taken in conjunction with the accompanying drawings. The holder of the present invention is described at pp.105-6 of *The Journal of Urology*, Vol. 138, Jul.1987, incorporated herein by reference.

BRIEF DESCRIPTION OF THE DRAWINGS

FIG. 3 is a partial perspective view of the clamp employed in the surgical holder of the present invention, the clamp being shown as supporting the shaft region of a cystoscope;

FIG. 4 is a cross-sectional view of the clamp assembly employed in the present invention shown in FIG. 3 taken along line 4—4 in FIG. 3;

FIG. 5 is a cross-sectional view of the clamp assembly shown in FIG. 4 taken along line 5—5 in FIG. 4; and FIG. 6 is an exploded elevational view of the clamp assembly of FIG. 3.

DETAILED DESCRIPTION OF THE PREFERRED EMBODIMENTS

Figure 1:
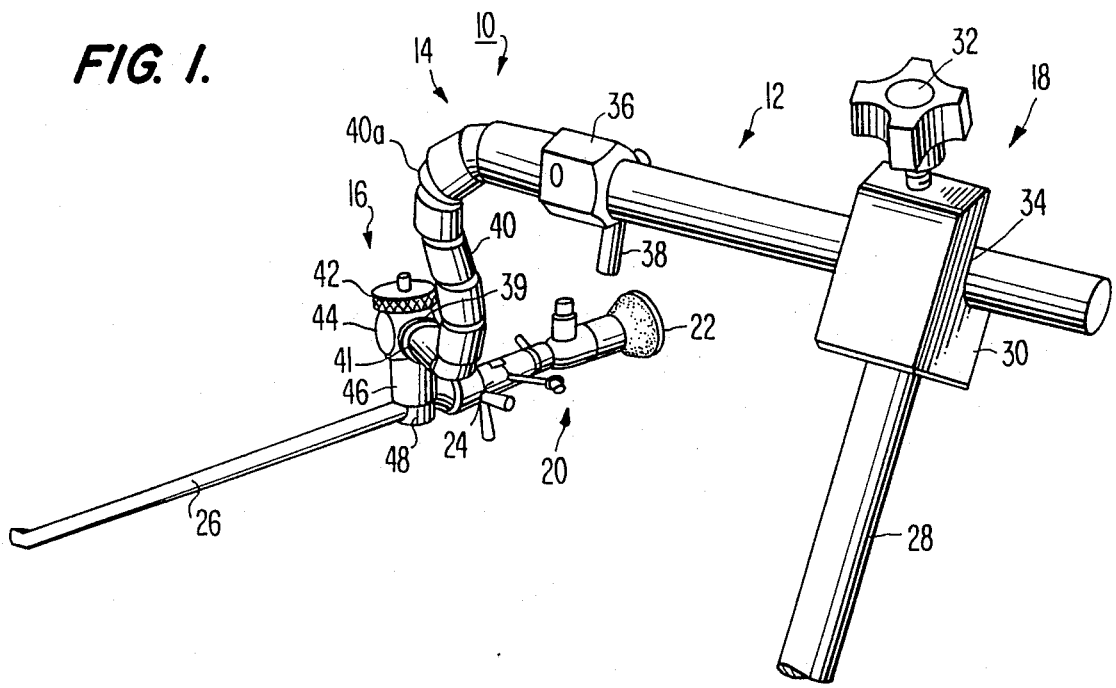
FIG. 1 is a perspective view of a surgical holder of the present invention supporting a cystoscope.

The presently preferred embodiment of the invention is shown in FIG. 1 of the drawings where a surgical holder 10 is shown to include a base rod 12, a flexible post 14, and a clamp assembly 16. The clamp 16 is shown holding a typical cystoscope 20 having an eyepiece 22, a control section 24 and a sheath or shaft 26. The base rod 12 of the holder 10 is attachable to an operating room table clamping assembly 18 provided with a vertical post 28, a cradle assembly 30, 34, and a screw adjustment knob 32, the cradle 34 being adapted to receive and hold the base rod 12 therein.

The base rod 12, generally of an elongated tubular configuration, is provided with a nut 36 at one end for receiving and mounting the flexible post 14. The nut is equipped with tightening lever 38 which in one position permits adjustment of the flexible post 14 to any position, thus allowing for three-dimensional movement. The base rod 12 is preferably formed of stainless steel material, but any suitable inert material may be employed, such as aluminum or rigid heat-resistant plastic, so long as the material possesses smooth and rigid characteristics, can be heat-sterilized, and presents no danger to the patient.

The flexible post 14 is equipped with a plurality of sections 40, suitably chrome-plated tubular steel, and precision ball joints 40a connected by an internally-positioned flexible cable (not shown), suitably formed of steel. Movement of the lever 38 to a second position shortens the flexible internal cable and locks the flexible post 14 into its pre-set position. It should be understood that while the preferred embodiment of the present invention utilizes chrome-plated, tubular steel sections for the flexible post 14, it is possible to employ other materials as well. For example, the flexible post 14 could be formed of inert, heat resistant rigid plastic materials, such as polyacetal or polycarbonate resin or the like. The flexible post 14 is equipped at its distal end i.e. the end opposing the end attached to the base rod 12, with a nut/screw assembly 41 (See FIG. 3) securing the clamp assembly 16 thereto.

The clamp assembly 16 includes a C-shaped, opensided member 48 for receiving the shaft 26 of the cystoscope 20 therein, a tubular housing 46, a head portion 44, and a tightening knob 42. The clamp assembly 16 permits 360 degree rotation of the cystoscope about an axis parallel to or concentric with the distal end of the flexible post 14, by rotation about the axis of a connecting stem 39 (see FIGS. 3 and 4). The clamp assembly members 42, 44, 46, 48 are preferably formed of stainless steel materials; however, it should be understood that other materials which are inert and heat-sterilizable and possess sufficient strength and rigidity are also suitable, such as aluminum and certain plastic materials.

Figure 2:
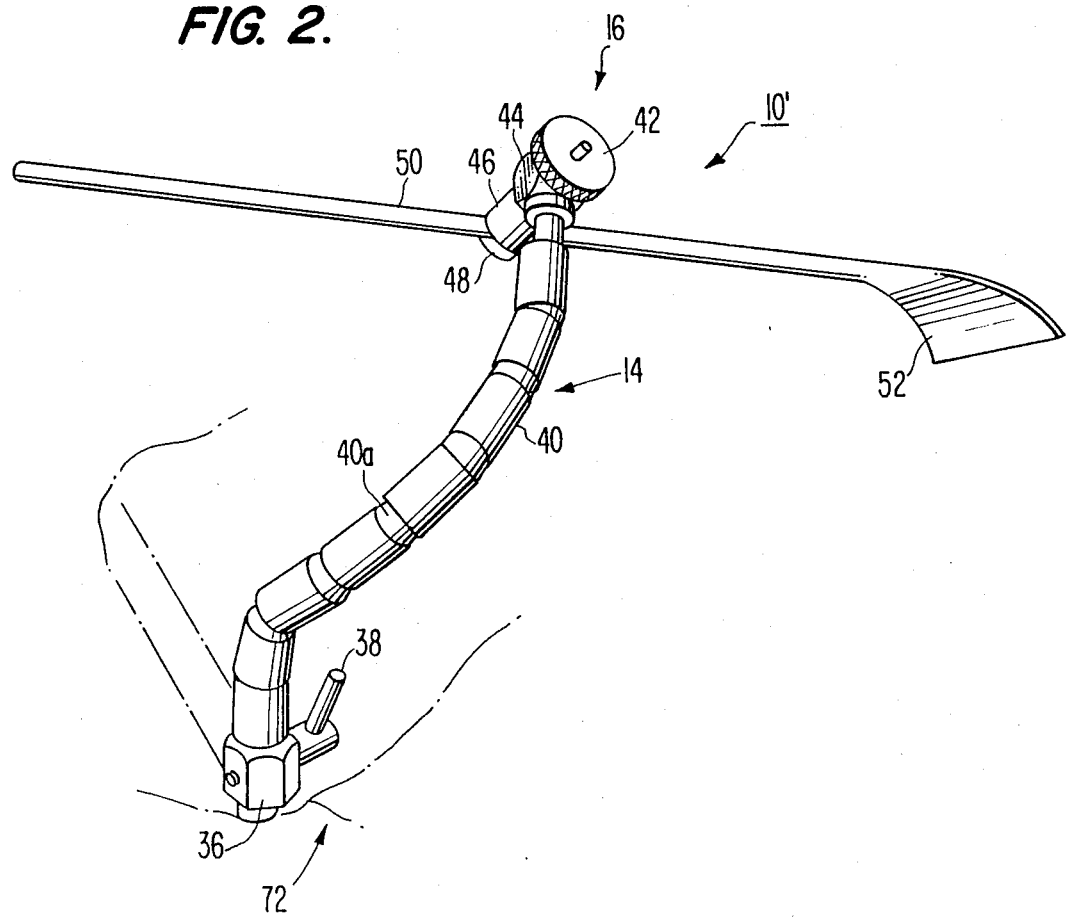
FIG. 2 is a perspective view of the surgical holder of the present invention, the holder being shown for supporting a surgical retractor.

Referring now to FIG. 2 of the drawings, there is shown an identical or similar holder 10' compared to the holder 10 of FIG. 1. Here, however, the holder 10' is shown holding and positioning a surgical retractor 50 having a curved portion 52 at one end thereof. The holder 10' includes all the elements described above in relation to the holder 10 of FIG. 1, the device being supported by any suitable region of an operating table 72. It should be understood that the clamp assembly 16, more particularly the C-shaped member 48 which is spring-biased to the open position, can accommodate various retractors, cystoscopes or other instruments of different diameters with minimum manipulation required by a user by simply turning the knurled knob 42.

Referring now to FIGS. 3-6 of the drawings, which illustrate the proposed clamping assembly 16 employed in the present invention, it is seen that the head portion 44 is provided with a central cavity 44a, a top centrally aligned opening 44b which is in communication with the central cavity 44a, and a bottom centrally aligned opening 44c having a somewhat tapered or slanted or frustoconical wall 44d, the opening 44c also being in communication with the central cavity 44a. The wall 44d of the bottom opening 44c generally tapers outwardly and downwardly from the central cavity 44a toward the exterior of the head portion 44. Openings 44b and 44c and the central cavity 44a should be in vertical longitudinal alignment, i.e. all should share the same longitudinal axis. It will be understood that the terms "top" and "bottom" refer to the attitude of the device as shown in FIGS. 3, 4 and 6, but that in use the clamp 16 may be oriented in other attitudes.

The tapered region 44d of the bottom opening 44c is adapted to receive a hollow tabular clamp housing 46 which includes a top plate 46c, having an integrally formed somewhat beveled wall 46a complementary in shape with, and recessed within, the frustoconical wall 44d of the head portion 44. The top plate 46c has a slot opening 46d extending therethrough. The tubular clamp housing 46 suitably has a diameter substantially equal to or less than the diameter of the bottom opening 44c of the head portion 44, so that the clamp housing 46 may easily and snugly fit within the bottom opening 44c. The housing 46 is adapted to rotate about its axis relative to the head portion 44 by sliding movement between the tapered complementary surfaces 44c and 46a.

As best seen in FIGS. 4 and 6 of the drawings, the tubular housing 46 is adapted to receive within its hollow interior the C-shaped, open-sided member 48, which includes a C-shaped jaw portion 49 located along the longitudinal axis of the housing 46 and head portion 44, a central portion 48a of reduced cross-section relative to the jaw portion 49, and a still smaller in cross-section threaded shaft portion 43a. The central portion 48a, which has two opposite flat walls 48d and projects in a fitting relationship through the slot 46d of the top plate 46a of the housing 46, is integrally disposed between the threaded shaft portion 43a and the jaw portion 49. A coiled spring 48b is also provided within the housing 46 about the central portion 48a with its top end bearing against the inside of the top plate 46c and its bottom end bearing against the top of the jaw portion 49 along a ledge 48c. The coiled spring 48b thus urges the member 48 downwardly to an open position of the jaw 49. The C-shaped, open-sided jaw portion 49 is thus capable of receiving the sheath or shaft 26 of the cystoscope 20 (See FIG. 3), and indeed it should be understood that the C-shaped jaw 49 formed in portion 48 is capable of receiving various diameter-sized cystoscope or endoscope shafts, as long as the diameter of such a shaft does not exceed the space between portions 49a and 49b of the jaw 49.

As best illustrated in FIG. 6 of the drawings, the bottom of the tubular housing 46 includes a pair of circumferentially opposing notches 46e, only one of which is illustrated. These notches 46e aid in the clamping of the shaft 26 (See also FIG. 4) or the retractor 50 as in FIG. 2. Once a shaft has been inserted within the C-shaped region 49 and the device tightened as described below, the shaft is actually sandwiched between the lower portion of C-shaped region and the notches 46e, 46e located at the bottom end of the tubular housing 46. The inside clamping surfaces are shaped complementary to the shape of the instrument shaft being stabilized, so there is no problem of crushing or other damage to the instrument, while at the same time maintaining a good, solid clamping action.

The parts are assembled as shown in FIG. 6 with the member 48 being received within its housing 46 by positioning the coiled spring 48b about the central portion 48a (see particularly FIG. 4) and by inserting the entire structure longitudinally through the housing 46 as well as the head portion 44 and a stepped washer 42b. The threaded shaft portion 43a, once positioned within the top opening 44b of the head portion 44 and through the stepped washer 42b, is secured to the head portion 44 through the use of a screw adjustment knob 42 having a downwardly protruding tapered region 42a which is seated on the stepped washer 42b in the top opening 44b of the head portion 44. The upper end of the threaded shaft portion 43a is provided with an internally threaded countersink or bored out region 43b for receiving a conventional screw or bolt 43. The screw 43 acts as a stop for keeping the adjustment knob continually positioned on the threaded shaft 43a. The adjustment knob 42, which desirably has a knurled outer surface for easy grasping, is particularly easily used for closing the jaw 49 against the action of the spring 48b to hold the endoscope 26 or retractor 50 in place.

Referring now to FIGS. 3 and 6 of the drawings, the head portion 44 also includes the integrally formed annular projecting region or connecting stem 39 for receiving the distal end of the flexible post 14, which is easily secured through the use of a nut 41. As indicated above, the connecting stem 39 provides for a first 360° rotation about its axis of the clamp 16. Furthermore rotation of 360° is also provided about the axis of the member 48 and the housing 46 moving as a unit by sliding motion between the beveled surfaces 44c and 46a, this second 360° rotation being about a second axis 90° from the first axis of rotation. Tightening of the clamp 48 about the instrument shaft 26, 50 does not tighten the housing 46 against the head portion 44, and consequently does not inhibit rotation about the second axis.

It should be understood that the holder and clamp assembly of the present invention is particularly useful for holding cystoscopes or other endoscopes or surgical retractors or the like even after these instruments have been positioned relative to the patient, and that this capability greatly facilitates manipulation by a surgeon or other physician. With the clamp biased in an open position and the instrument already positioned relative to the patient in the desired position, the holder is easily moved into position adjacent the shaft of the instrument and the instrument is moved sideways into the C-shaped region 49 where it is clamped by rotation of the knob 42. Because the size of the opening of the clamp is determined by the position of the knurled knob 42 along the length of the thread of the threaded shaft 43a, it will be understood that the size of the clamp opening when closed about the shaft or sheath 26 is finely controllable.

Moreover, the holder and clamp assembly is flexible and permits 360 degree rotation of the clamp assembly about two axes located at right angles to one another at the region where the clamping assembly is connected to the flexible post. The system is relatively simple and inexpensive to manufacture and requires little manual manipulation to use, this freeing the surgeon's or other physician's hands for other more important operations.

It will be obvious to those skilled in the art that various other changes and modifications may be made without departing from the scope of the invention and the invention is not to be considered limited to what is shown in the drawings and described in the specification.

What is claimed is:

1. A flexible holder, particularly suited for adjustably mounting and stabilizing a cystoscope or other endoscopic instrument having an elongated shaft comprising:

an elongated horizontally extending base rod having a fixable end and a connectable end;

an elongated flexible post having a clamping end and a connectable end, said clamping end being releasably connected to said connectable end of said base rod; and a clamping assembly for holding the shaft of said instrument and first means for rotatably connecting said clamping assembly to said connectable end of said flexible post about a first axis, said clamping assembly, comprising:

a C-shaped, open-sided clamping jaw having an integrally formed, vertically extending upper portion;

a tubular housing for axially slidably receiving said clamping jaw therein, and having an open beveled top wall and an open bottom wall, said bottom wall having circumferentially opposing notches therein, said tubular housing and said clamping jaw being rotatable about a second axis passing therethrough, said second axis being disposed 90° from said first axis;

a head portion having an open top wall, an open bottom wall, and an internal centrally-located cavity;

spring means, positioned between said top wall of said tubular housing and said clamping jaw when said clamping jaw is situated within said tubular housing for biasing said clamping jaw in a downward vertical direction; and variable tightening means for axially moving said clamping jaw to a selected position into said tubular housing against the force of said spring means to urge said C-shaped, open-sided clamping jaw against an instrument shaft to abut against said notches of said tubular housing to hold the instrument within said clamping assembly, and without tightening said first means for rotatably connecting said clamping assembly to said flexible post about said first axis.

2. A flexible holder in accordance with claim 1, wherein said vertically extending upper portion of said clamping jaw includes a longitudinally aligned threaded shaft portion integrally formed to a longitudinally aligned central portion, said upper portion being inserted and encased within said head portion and said central portion being inserted and encased within said tubular housing.

3. A flexible holder in accordance with claim 1, wherein said open bottom wall of said head portion includes an opening having an annular downwardly and outwardly tapering wall for receiving therein said open beveled top wall of said tubular housing.

4. A flexible holder in accordance with claim 1, wherein said clamping jaw includes an upper ledge which serves as an abutment for the lower portion of said spring means.

5. A holder for adjustably holding and stabilizing an instrument having an elongated shaft after positioning the instrument relative to a patient, comprising:

an elongated flexible post for fixedly mounting at a situs of surgery or examination, and having a proximal mounting end and a distal supporting end; and a clamping assembly and first means for rotatably connecting said clamping assembly about a first axis to said distal supporting end of said flexible post, said clamping assembly including (1) a head portion having a bore extending therethrough along a second axis generally perpendicular to said first axis, and a first bracing and sliding surface adjacent a first end of the bore;

(2) a tubular housing axially aligned with the bore of said head portion and having a second bracing and sliding surface for mating with said first bracing and sliding surface, whereby said tubular housing can rotate relative to said head portion about the second axis;

(3) an axially reciprocable clamping member mounted for axial movement within said tubular housing and said head portion along the second axis, said clamping member having (i) a C-shaped open jaw portion projecting from an end of said tubular housing opposite said second bracing and sliding surface, said jaw portion having an outside size and configuration corresponding to the inside of said tubular housing;

(ii) a central portion of reduced cross-sectional size compared to said jaw portion and axially attached thereto, said central portion being at least partly received within said tubular housing and being fixed against relative rotation with said tubular housing; and (iii) a threaded shaft portion axially attached to said central portion and partly received within the bore of said head portion;

(4) spring means, positioned within said tubular housing and about said central portion of said clamping member, for biasing said jaw portion out of said tubular housing; and (5) tightening means on said threaded shaft for axially moving said jaw portion into said tubular housing against the force of said spring means and without tightening said first means for rotatably connecting said clamping assembly to said flexible post.

6. A holder according to claim 5 wherein said first bracing and sliding surface of said head portion comprises a first frustoconical wall, and said second bracing and sliding surface of said tubular housing comprises a second frustoconical wall at an end of said tubular housing, said second frustoconical wall being complementary to said first frustoconical wall.

7. A holder according to claim 5 wherein said tubular housing has a circular cylindrical inner wall and said C-shaped open jaw portion has a circular cylindrical outer wall.

8. A holder according to claim 5 wherein said tubular housing has a cover plate at its end adjacent said head portion, said cover plate having a radially projecting slot extending therethrough, said central portion of said clamping member being shaped complementary to said slot and extending therethrough to effect said fixation against relative rotation of said tubular housing and said central portion.

9. A holder according to claim 5 wherein said spring means is a coil spring which surrounds said central portion of said clamping member.

10. A holder according to claim 5 wherein said tightening means comprises a knob adjacent a second end of the bore of said head portion, said knob being screw threaded on said threaded shaft.

11. A holder according to claim 10 further comprising a stepped washer mounted about said threaded shaft between said knob and said head portion.

12. A holder according to claim 5 wherein said tubular housing comprises a pair of circumferentially opposing notches at an end thereof opposite said second bracing and sliding surface, said notches cooperating with said C-shaped open jaw portion to hold therebetween a cylindrical shaft of an instrument.

13. A flexible holder in accordance with claim 1 wherein said C-shaped, open-sided clamping jaw comprises a C-shaped clamping portion, said second axis passing through said C-shaped clamping portion.

14. A holder in accordance with claim 5 wherein said C-shaped open jaw portion is located along said second axis.

15. A holder for adjustably holding and stabilizing an instrument having an elongated shaft after positioning the instrument relative to a patient, comprising:
- an elongated flexible post for fixedly mounting at a situs of surgery or examination, and having a proximal mounting end and a distal supporting end; and
- a clamping assembly and first means for rotatably connecting said clamping assembly about a first axis to said distal supporting end of said flexible post, said clamping assembly including clamping-member-supporting means for holding and supporting said clamping member, comprising a hollow tubular member having an annular bottom wall constituting a jaw member in the form of a pair of notches spaced about 180° from one another about said annular bottom wall,
- said clamping assembly further including an axially reciprocable clamping member mounted for axial movement within said hollow tubular member of said clamping-member-supporting means along a second axis generally perpendicular to said first axis, said clamping means having a generally C-shaped open jaw portion aligned with said second axis and opposing said jaw member; and
- said clamping assembly further comprises spring means positioned within said clamping-member-supporting means for biasing said C-shaped open jaw portion away from said jaw member; and tightening means for axially moving said axially reciprocal clamping member toward said jaw member against the force of said spring means and without tightening said first means for rotatably connecting said clamping assembly to said flexible post.

* * * * *